United States Patent
Xue et al.

(10) Patent No.: US 10,436,563 B2
(45) Date of Patent: Oct. 8, 2019

(54) COMPREHENSIVE CHECKING FIXTURE FOR STEERING KNUCKLE

(71) Applicant: CITIC Dicastal CO., LTD, Qinhuangdao (CN)

(72) Inventors: Bowen Xue, Qinhuangdao (CN); Jiandong Guo, Qinhuangdao (CN)

(73) Assignee: CITIC Dicastal CO., LTD, Qinhuangdao (CN)

( * ) Notice: Subject to any disclaimer, the term of this patent is extended or adjusted under 35 U.S.C. 154(b) by 212 days.

(21) Appl. No.: 15/636,752

(22) Filed: Jun. 29, 2017

(65) Prior Publication Data
US 2018/0003475 A1 Jan. 4, 2018

(30) Foreign Application Priority Data

Jun. 29, 2016 (CN) .......................... 2016 1 0491967

(51) Int. Cl.
| | |
|---|---|
| *G01B 5/25* | (2006.01) |
| *G01B 5/00* | (2006.01) |
| *G01B 5/14* | (2006.01) |
| *G01N 29/44* | (2006.01) |
| *G08C 21/00* | (2006.01) |
| *G01B 3/14* | (2006.01) |

(52) U.S. Cl.
CPC ......... *G01B 5/0009* (2013.01); *G01B 5/0004* (2013.01); *G01B 5/0025* (2013.01); *G01B 5/143* (2013.01); *G01B 3/14* (2013.01); *G01N 29/4472* (2013.01); *G08C 21/00* (2013.01)

(58) Field of Classification Search
CPC ................................... G01B 5/0025
USPC ......................................... 33/1 BB
See application file for complete search history.

(56) References Cited

U.S. PATENT DOCUMENTS

| | | | | | |
|---|---|---|---|---|---|
| 2,911,727 | A | * | 11/1959 | Steinhart | G01B 5/0025 33/533 |
| 3,869,804 | A | * | 3/1975 | Friend | G01B 5/0025 33/288 |
| 4,549,359 | A | * | 10/1985 | Hense | G01B 5/0025 33/1 M |
| 5,026,033 | A | * | 6/1991 | Roxy | B23Q 3/103 269/309 |
| 5,107,599 | A | * | 4/1992 | Marincic | G01B 5/0004 269/309 |
| 5,829,151 | A | * | 11/1998 | Collier | B23Q 7/14 33/573 |

(Continued)

*Primary Examiner* — Christopher W Fulton
(74) *Attorney, Agent, or Firm* — Maier & Maier, PLLC

(57) ABSTRACT

A checking fixture for a steering knuckle. In use, a workpiece is mounted on the checking fixture, three locating points of the workpiece in the X direction respectively correspond to a supporting pin I, a supporting pin II and a supporting pin III, a locating taper hole limiting the motion of the workpiece in a YZ plane corresponds to the floating pin, and a locating point of the workpiece in the Y direction levelly fit to a supporting surface of a locating pin; after location is completed, the workpiece is tightly clamped by a jacking clamp, a press clamp I and a press clamp II. The checking fixture for the steering knuckle can measure the position accuracy of each hole of the steering knuckle workpiece, and can detect whether the relative height of the flange plane of the workpiece relative to the X-direction locating points is qualified.

4 Claims, 2 Drawing Sheets

(56) References Cited

U.S. PATENT DOCUMENTS

| | | | | |
|---|---|---|---|---|
| 5,883,313 | A | * | 3/1999 | Ercole .................. G01B 5/0004 33/504 |
| 6,145,212 | A | * | 11/2000 | Geise ..................... G01B 5/207 33/529 |
| 8,800,156 | B2 | * | 8/2014 | Sullivan .................. G01B 3/14 33/1 BB |
| 9,879,966 | B2 | * | 1/2018 | Xue ..................... G01B 5/0004 |
| 2005/0235510 | A1 | * | 10/2005 | Ly ........................ G01B 5/0004 33/549 |
| 2007/0294899 | A1 | * | 12/2007 | Li ..................... G01B 11/0691 33/1 BB |
| 2016/0200356 | A1 | * | 7/2016 | Xue ........................ B62D 7/18 29/428 |

\* cited by examiner

COMPREHENSIVE CHECKING FIXTURE FOR STEERING KNUCKLE

TECHNICAL FIELD

The present invention relates to a checking fixture, and in particular to a comprehensive checking fixture for checking the position accuracy of a steering knuckle and the height of a flange plane

BACKGROUND ART

A steering knuckle of an automobile is a very important component for the automobile, its machining process is very complex, and different components are mounted in different holes of the steering knuckle in a combination manner. Therefore, the position accuracy of each hole is very important. In order to monitor whether the position accuracy of each hole is qualified during production, currently a position accuracy comprehensive checking fixture is utilized in the industry. Such checking fixture has higher detection efficiency and is more convenient to detect compared with a three-coordinate measuring machine.

SUMMARY OF THE INVENTION

An object of the present invention is to provide a comprehensive checking fixture for a steering knuckle, which can simultaneously measure the position accuracy of each hole of a steering knuckle workpiece, and can detect whether the relative height of a flange plane of the workpiece relative to X-direction locating points is qualified.

To achieve the object described above, a technical solution of the present invention is as follows: a comprehensive checking fixture for a steering knuckle is composed of landing legs, a base plate, a support I, a detection pin I, a guide sleeve I, a supporting pin I, a detection board, a standard ring, a detection pin II, a guide sleeve II, a floating pin, a keyway, a spring, a gasket, a supporting pin II, a supporting pin III, a support II, a locating pin, a jacking clamp, a press clamp I and a press clamp II. Four landing legs are fixed on the lower surface of the base plate; the guide sleeve I is mounted on the support I, the support I is fixed on the left side of the upper surface of the base plate, and the detection pin I matches with the guide sleeve I; the supporting pin I, the supporting pin II and the supporting pin III are all fixed at corresponding positions of the upper surface of the base plate, and such positions correspond to positions of three locating points of a workpiece in the X direction; the locating pin is fixed on the support II, the support II is also fixed at a corresponding position of the upper surface of the base plate, and the tail end of the locating pin corresponds to a position of a locating point of the workpiece in the Y direction; the jacking clamp, the press clamp I and the press clamp II are each fixed above the upper surface of the base plate through a supporting seat, and the jacking clamp and the locating pin are coaxial; the guide sleeve II is fixed on the base plate, and the axial line of the guide sleeve II and the theoretical axial direction of a workpiece center bore are coaxial; the detection pin II matches with the guide sleeve II, and the gasket is fixed at the bottom of the detection pin II; the standard ring is mounted on the upper surface of the base plate, and the detection board is used for detecting the height of the flange plane of the workpiece when matching with the top surface of the standard ring; the floating pin matches with the keyway and is mounted in the keyway through the nether spring; and the keyway is fixed on the upper surface of the base plate, and the position of the axial line of the keyway corresponds to a locating point, limiting the motion of the workpiece in a YZ plane, of the workpiece.

The flatness of the upper end face of the standard ring is smaller than 0.005 mm. A fit clearance between the detection pin I and the guide sleeve I and a fit clearance between the detection pin II and the guide sleeve II respectively are 0.005 mm.

The detection board is step-type, the front end of the detection board is allowance above nominal size of the height of the flange plane in the X direction, and the back end of the detection board is allowance below nominal size of the height of the flange plane in the X direction.

During actual use, the workpiece is mounted on the checking fixture, the three locating points of the workpiece in the X direction respectively correspond to the supporting pin I, the supporting pin II and the supporting pin III, a locating taper hole limiting the motion of the workpiece in the YZ plane corresponds to the floating pin, and the locating point of the workpiece in the Y direction levelly fit to a supporting surface of the locating pin; after location is completed, the workpiece is tightly clamped by the jacking clamp, the press clamp I and the press clamp II; the detection pin I is inserted into a corresponding to-be-detected hole of the workpiece, and if the detection pin I can be inserted into the corresponding to-be-detected hole of the workpiece, the position accuracy of the to-be-detected hole of the workpiece is qualified; the detection pin II is lifted up, and if the detection part of the detection pin II can be inserted into a to-be-detected center bore of the workpiece, the position accuracy of the to-be-detected center bore of the workpiece is qualified; and the detection board is inserted into a clearance between the flange plane of the workpiece and the upper end face of the standard ring, and if a go end of the detection board passes through the clearance and a no go end of the detection board does not pass through the clearance, the height of the flange plane of the workpiece is qualified.

In use, the comprehensive checking fixture for the steering knuckle, provided by the present invention, can simultaneously measure the position accuracy of each hole of the steering knuckle workpiece, and can detect whether the relative height of the flange plane of the workpiece relative to the X-direction locating points is qualified; and meanwhile, the comprehensive checking fixture for the steering knuckle has the characteristics of simple structure, high detection precision, safe and stable performances, low manufacturing costs and the like.

Figures 1, 2:
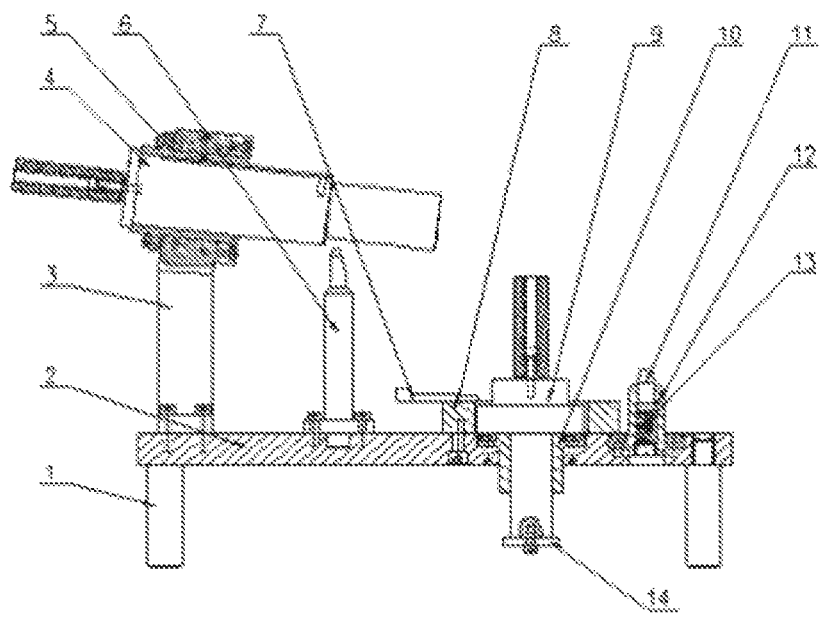
FIG. 1 is a front view of a comprehensive checking fixture for a steering knuckle, provided by the present invention.
FIG. 2 is a left view of a comprehensive checking fixture for a steering knuckle, provided by the present invention.
Figure 3:
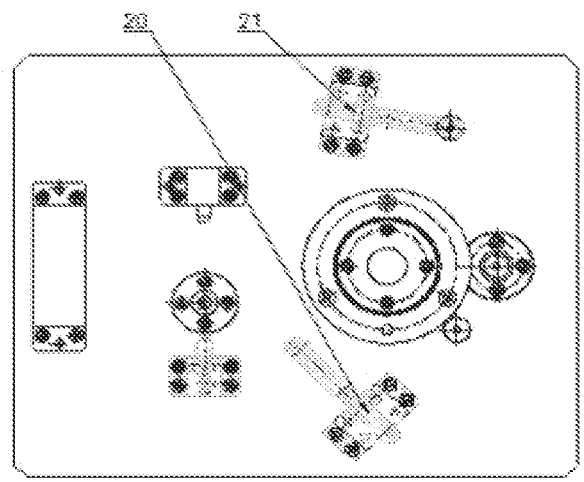
FIG. 3 is a top view of a comprehensive checking fixture for a steering knuckle, provided by the present invention.
Figure 4:
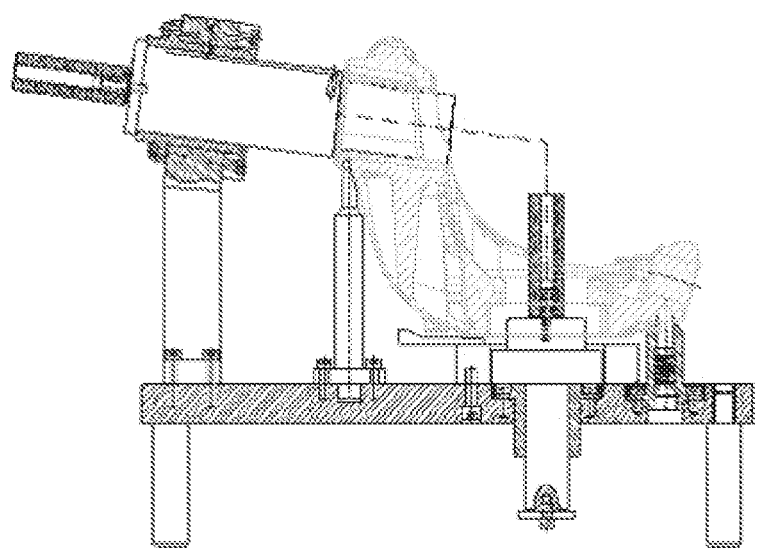
FIG. 4 is a front view of a comprehensive checking fixture for a steering knuckle, provided by the present invention, after a workpiece is clamped.

In the figure, numeric symbols are as follows: 1—landing leg, 2—base plate, 3—support I, 4—detection pin I, 5—guide sleeve I, 6—supporting pin I, 7—detection board, 8—standard ring, 9—detection pin II, 10—guide sleeve II, 11—floating pin, 12—keyway, 13—spring, 14—gasket, 15—supporting pin II, 16—supporting pin III, 17—support II, 18—locating pin, 19—jacking clamp, 20—pressing clamp I, and 21—pressing clamp II.

DETAILED DESCRIPTION OF THE INVENTION

In the following, the details and working conditions of a specific device provided by the present invention are described in combination with figures.

A comprehensive checking fixture for a steering knuckle is composed of landing legs 1, a base plate 2, a support I 3, a detection pin I 4, a guide sleeve I 5, a supporting pin I 6, a detection board 7, a standard ring 8, a detection pin II 9, a guide sleeve II 10, a floating pin 11, a keyway 12, a spring 13, a gasket 14, a supporting pin II 15, a supporting pin III 16, a support II 17, a locating pin 18, a jacking clamp 19, a press clamp I 20 and a press clamp II 21. Four landing legs 1 are fixed on the lower surface of the base plate 2; the guide sleeve I 5 is mounted on the support I 3, the support I 3 is fixed on the left side of the upper surface of the base plate 2, and the detection pin I 4 matches with the guide sleeve I 5; the supporting pin I 6, the supporting pin II 15 and the supporting pin III 16 are all fixed at corresponding positions of the upper surface of the base plate 2, and such positions correspond to positions of three locating points of a workpiece in the X direction; the locating pin 18 is fixed on the support II 17, the support II 17 is also fixed at a corresponding position of the upper surface of the base plate 2, and the tail end of the locating pin 18 corresponds to a position of a locating point of the workpiece in the Y direction; the jacking clamp 19, the press clamp I 20 and the press clamp II 21 are each fixed above the upper surface of the base plate 2 through a supporting seat, and the jacking clamp 19 and the locating pin 18 are coaxial; the guide sleeve II 10 is fixed on the base plate 2, and the axial line of the guide sleeve II 10 and the theoretical axial direction of a workpiece center bore are coaxial; the detection pin II 9 matches with the guide sleeve II 10, and the gasket 14 is fixed at the bottom of the detection pin II 9; the standard ring 8 is mounted on the upper surface of the base plate 2, and the detection board 7 is used for detecting the height of a flange plane of the workpiece when matching with the top surface of the standard ring 8; the floating pin 11 matches with the keyway 12 and is mounted in the keyway 12 through the nether spring 13; and the keyway 12 is fixed on the upper surface of the base plate 2, and the position of the axial line of the keyway 12 corresponds to a locating point, limiting the motion of the workpiece in a YZ plane, of the workpiece.

The flatness of the upper end face of the standard ring 8 is smaller than 0.005 mm. A fit clearance between the detection pin I 4 and the guide sleeve I 5 and a fit clearance between the detection pin II 9 and the guide sleeve II 10 respectively are 0.005 mm.

The detection board 7 is step-type, the front end of the detection board 7 is allowance above nominal size of the height of the flange plane in the X direction, and the back end of the detection board 7 is allowance below nominal size of the height of the flange plane in the X direction.

In a working process, the workpiece is mounted on the checking fixture, the three locating points of the workpiece in the X direction respectively correspond to the supporting pin I 6, the supporting pin II 15 and the supporting pin III 16, a locating taper hole limiting the motion of the workpiece in the YZ plane corresponds to the floating pin 11, and the locating point of the workpiece in the Y direction levelly fit to a supporting surface of the locating pin 18; after location is completed, the workpiece is tightly clamped by the jacking clamp 19, the press clamp I 20 and the press clamp II 21; the detection pin I 4 is inserted into a corresponding to-be-detected hole of the workpiece, and if the detection pin I 4 can be inserted into the corresponding to-be-detected hole of the workpiece, the position accuracy of the to-be-detected hole of the workpiece is qualified; the detection pin II 9 is lifted up, and if the detection part of the detection pin II 9 can be inserted into a to-be-detected center bore of the workpiece, the position accuracy of the to-be-detected center bore of the workpiece is qualified; and the detection board 7 is inserted into a clearance between the flange plane of the workpiece and the upper end face of the standard ring, and if a go end of the detection board 7 passes through the clearance and a no go end of the detection board 7 does not pass through the clearance, the height of the flange plane of the workpiece is qualified.

The invention claimed is:

1. A comprehensive checking fixture for a steering knuckle, comprising:
    landing legs, a base plate, a support I, a detection pin I, a guide sleeve I, a supporting pin I, a detection board, a standard ring, a detection pin II, a guide sleeve II, a floating pin, a keyway, a spring, a gasket, a supporting pin II, a supporting pin III, a support II, a locating pin, a jacking clamp, a press clamp I and a press clamp II;
    wherein four landing legs are fixed on the lower surface of the base plate;
    the guide sleeve I is mounted on the support I, the support I is fixed on the left side of the upper surface of the base plate, and the detection pin I matches with the guide sleeve I;
    the supporting pin I, the supporting pin II and the supporting pin III are all fixed at corresponding positions of the upper surface of the base plate;
    the locating pin is fixed on the support II, the support II is also fixed at a corresponding position of the upper surface of the base plate, and the tail end of the locating pin corresponds to a position of a locating point of the workpiece in the Y direction;
    the jacking clamp, the press clamp I and the press clamp II are each fixed above the upper surface of the base plate through a supporting seat, and the jacking clamp and the locating pin are coaxial;
    the guide sleeve II is fixed on the base plate, and the axial line of the guide sleeve II and the theoretical axial direction of a workpiece center bore are coaxial;
    the detection pin II matches with the guide sleeve II, and the gasket is fixed at the bottom of the detection pin II;
    the standard ring is mounted on the upper surface of the base plate, and the detection board is used when matching with the top surface of the standard ring; the floating pin is mounted in the keyway through the spring; and
    the keyway is fixed on the upper surface of the base plate, and the position of the axial line of the keyway corresponds to a locating point, limiting the motion of the workpiece in a YZ plane, of the workpiece.

2. The comprehensive checking fixture for the steering knuckle according to claim 1, wherein the flatness of the upper end face of the standard ring is smaller than 0.005 mm.

3. The comprehensive checking fixture for the steering knuckle according to claim 1, wherein a fit clearance between the detection pin I and the guide sleeve I and a fit clearance between the detection pin II and the guide sleeve II respectively are 0.005 mm.

4. The comprehensive checking fixture for the steering knuckle according to claim 1, wherein the detection board is step-type, the front end of the detection board is allowance above nominal size of the height of the flange plane in the X direction, and the back end of the detection board is allowance below nominal size of the height of the flange plane in the X direction.

\* \* \* \* \*